US012564454B1

(12) United States Patent
Prada et al.

(10) Patent No.: US 12,564,454 B1
(45) Date of Patent: Mar. 3, 2026

(54) GENERATING MEDICAL INTELLIGENCE DATA USING KNOWLEDGE GRAPHS AND MACHINE LEARNING

(71) Applicant: CSATS, Inc., Seattle, WA (US)

(72) Inventors: Kenneth Fernandez Prada, San Jose, CA (US); Amer Ghanem, West Chester, OH (US); Huzefa Neemuchwala, Simi Valley, CA (US)

(73) Assignee: CSATS, INC., Seattle, WA (US)

( * ) Notice: Subject to any disclaimer, the term of this patent is extended or adjusted under 35 U.S.C. 154(b) by 314 days.

(21) Appl. No.: 18/342,262

(22) Filed: Jun. 27, 2023

Related U.S. Application Data

(60) Provisional application No. 63/357,617, filed on Jun. 30, 2022.

(51) Int. Cl.
| | |
|---|---|
| *A61B 34/00* | (2016.01) |
| *A61B 34/20* | (2016.01) |
| *G16H 10/60* | (2018.01) |
| *G16H 40/20* | (2018.01) |

(52) U.S. Cl.
CPC .............. *A61B 34/25* (2016.02); *A61B 34/20* (2016.02); *G16H 10/60* (2018.01); *G16H 40/20* (2018.01); *A61B 2034/2055* (2016.02); *A61B 2034/252* (2016.02); *A61B 2034/254* (2016.02); *A61B 2034/256* (2016.02)

(58) Field of Classification Search
None
See application file for complete search history.

(56) References Cited

U.S. PATENT DOCUMENTS

| | | | | | |
|---|---|---|---|---|---|
| 10,572,734 | B2 * | 2/2020 | Alvi | ....................... | G06V 20/49 |
| 2006/0142657 | A1 * | 6/2006 | Quaid | ................... | A61B 90/37 |
| | | | | | 600/424 |
| 2007/0136218 | A1 * | 6/2007 | Bauer | ................... | G16H 50/20 |
| | | | | | 700/83 |
| 2023/0027978 | A1 * | 1/2023 | Gaborit | ................. | G16H 50/20 |

* cited by examiner

*Primary Examiner* — Michael W Kahelin
(74) *Attorney, Agent, or Firm* — Amsel IP Law PLLC; Jason Amsel

(57) ABSTRACT

A medical intelligence system generates medical assistance data determined to be relevant to an ongoing medical procedure. A state inference engine obtains medical video data and/or sensor data from sensors during the medical procedure and generates recognition data indicative of a state of the medical procedure. A medical procedure intelligence engine accesses a knowledge graph populated from multiple disparate sources and determines, based on a medical intelligence model, the medical assistance data based on the recognition data and the information in the knowledge graph. The knowledge graph and the medical intelligence model may be updated as additional knowledge and medical data is learned. The medical intelligence system may generate information such as, for example, video clips or instructions relating to a next step in the medical procedure, billing codes or descriptions of the medical procedure for medical records, and/or other data characterizing performance of the medical procedure.

18 Claims, 9 Drawing Sheets

Retrive Patient Data 102

Create Pre-Planning Anatomical Models 104

Identify and Tag Structures 106

Track and Guide Medical Steps 108

Manage and Store Surgical Videos and Sensor Data 110

Assess and Review Performance 112

Computing and Storage Environment 300

On-Site Storage and Processing 384

Remote Storage and Processing 386

Network 330

Local Processing Device 382

Obtain Video Data and Sensor Data Associated with Medical Procedure
902

Determine Recognition Data Characterizing Current State
904

Determine Medical Assistance Data Relevant to Current State
908

Present Surgical Assistance Data
910

GENERATING MEDICAL INTELLIGENCE DATA USING KNOWLEDGE GRAPHS AND MACHINE LEARNING

CROSS-REFERENCE TO RELATED APPLICATIONS

This application claims the benefit of U.S. Provisional Application No. 63/357,617 filed on Jun. 30, 2022, which is incorporated by reference herein.

BACKGROUND

Technical Field

The described embodiments relate to determining and providing contextual medical assistance for medical procedures.

Description of the Related Art

Medical procedures may include surgery such as minimally invasive surgery, biopsies, etc., and non-invasive procedures such as diagnosis, testing, etc. Medical procedures can be complex and may involve substantial expertise and experience. Because of the high stakes involved and the wide variety of situations that may arise, even the most skilled surgeons may benefit from quick and efficient access to relevant domain knowledge during the course of a medical procedure.

SUMMARY

Figure 1:
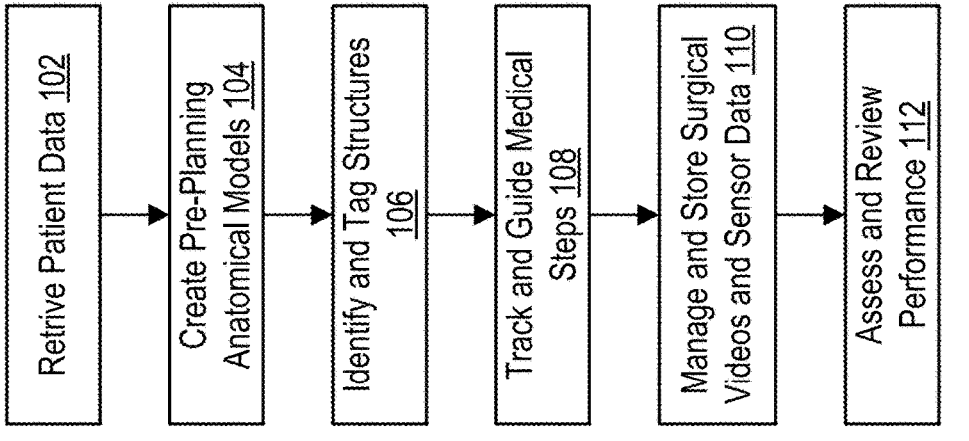
FIG. 1 is a flowchart illustrating an example process associated with a medical intelligence system.

In a first embodiment, a method provides intelligent medical assistance. Video data capturing a medical procedure and sensor data from one or more sensors associated with the medical procured are obtained during the medical procedure. Based on the video data and the sensor data, recognition data is determined that is indicative of a current state of the medical procedure. Medical assistance data is determined that is relevant to the current state of the medical procedure based on a medical intelligence model and a knowledge graph. An output device outputs the medical assistance data.

In an embodiment, determining the medical assistance data comprises determining a recommended next step in the medical procedure that follows from the current state, and obtaining, based on the recommended next step, a video clip associated with the recommended next step.

In an embodiment, determining the medical assistance data comprises determining a recommended next step in the medical procedure that follows from the current state, and obtaining, based on the recommended next step, documents or audio instructions associated with the recommended next step.

In an embodiment, determining and outputting the medical assistance data comprises identifying a medical billing code associated with the current state, and associating the medical billing code with a billing record in an electronic patient file.

In an embodiment, determining and outputting the medical assistance data comprises identifying a relevant form description associated with the current state of the medical procedure, and associating the relevant form description with an electronic patient file.

In an embodiment, the method further comprises training the medical intelligence model based on a history of medical procedure states associated with prior medical procedures and input responsive to prior medical assistance data.

In an embodiment, the knowledge graph comprises entities and relations derived from at least one of: an indexed video library, domain knowledge including medical literature, device characteristics, and key opinion leader workflows, and machine learning intelligence including patient data and surgeon data.

In an embodiment, the recognition data comprises step recognition data representing a current step of the medical procedure derived from at least one of the video data and sensor data, event recognition data representing an occurrence of an event associated with at least one of the video data and sensor data, and anatomy recognition data representing a detected anatomy associated with at least one of the video data and sensor data.

In a further embodiment, a non-transitory computer-readable storage medium stores instructions that when executed by one or more processors causes the one or more processors to perform any of the methods described above. In yet another embodiment, a computer system includes one or more processors and a non-transitory computer-readable storage medium as described above.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made to several embodiments, examples of which are illustrated in the accompanying figures. Wherever practicable, similar or like reference numbers may be used in the figures and may indicate similar or like functionality.

A medical intelligence system may provide contextual medical assistance that is determined to be relevant to an ongoing medical procedure. In some embodiments, determination may involve a priori determination (e.g., prediction) of assistance that may be helpful to a medical professional. For example, a state inference engine may obtain medical images (including preoperative, intraoperative, and video information) and/or sensory input from medical instruments (e.g. from (a) bio-medical sensors such as heart rate monitors, blood pressure readings, and other health related information as well as (b) instrument sensors, which may indicate the state of instruments during the medical procedure, etc.) and may generate state recognition data indicative of an expected or predicted state of the medical procedure. In some embodiments, a medical procedure intelligence engine may access a knowledge graph populated from multiple disparate sources and determine, based on an existing medical intelligence model, the medical assistance data based on the recognition data and the information in the knowledge graph. In some embodiments, the medical procedure model may be specific to the type of procedure being performed (e.g., as determined from patient, hospital, and/or other preoperative data).

In some embodiments, the knowledge graph and the medical intelligence model may be updated as additional knowledge and medical data is obtained. For example, data obtained during procedures may be used for training the medical intelligence model. The medical intelligence system may generate information such as, for example, context specific video clips or instructions relating to a determined next step in the medical procedure, billing codes or descriptions of the medical procedure for medical records, and/or other data characterizing performance of the medical procedure. The specificity of context may be procedural (specific to the procedure—e.g., navigating a robotic device to a specific section of an organ), specific to a step in the procedure (e.g., ablation), and/or specific to conditions (e.g., critical structures such as blood vessels, or tissue) detected in images obtained during the procedure.

FIG. 1 illustrates an example set of operations performed by a medical intelligence system that may be associated with various stages of a surgical procedure such as a pre-operative stage, an intra-operative stage, and a post-operative stage The medical intelligence system may automatically retrieve 102 patient data (e.g., from an electronic medical records (EMR) and/or picture archiving and communication system (PACS) database) and automatically create 104 pre-planning anatomical models for the patient based on the patient's medical history and pre-operative imaging. In an example operation, these steps 102, 104 could be performed in the pre-operative stage. The medical intelligence system may automatically identify and tag 106 structures within a field of view of imaging devices in the operating environment. This information may be displayed on a screen in the operating room for reference by a physician and staff. The medical intelligence system may furthermore automatically track 108 the steps of the surgical procedure and provide medical guidance associated with current and anticipated subsequent steps. In an example operation, these steps 106, 108 could be performed in the intra-operative stage. The medical intelligence system may also manage and store 110 surgical videos and other sensor data associated with the procedure, and automatically assess and review 112 performance of the physician and/or other staff. The information may be used to improve performance associated with future procedures. In an example operation, these steps 110, 112 could be performed in the post-operative stage.

Figure 2:
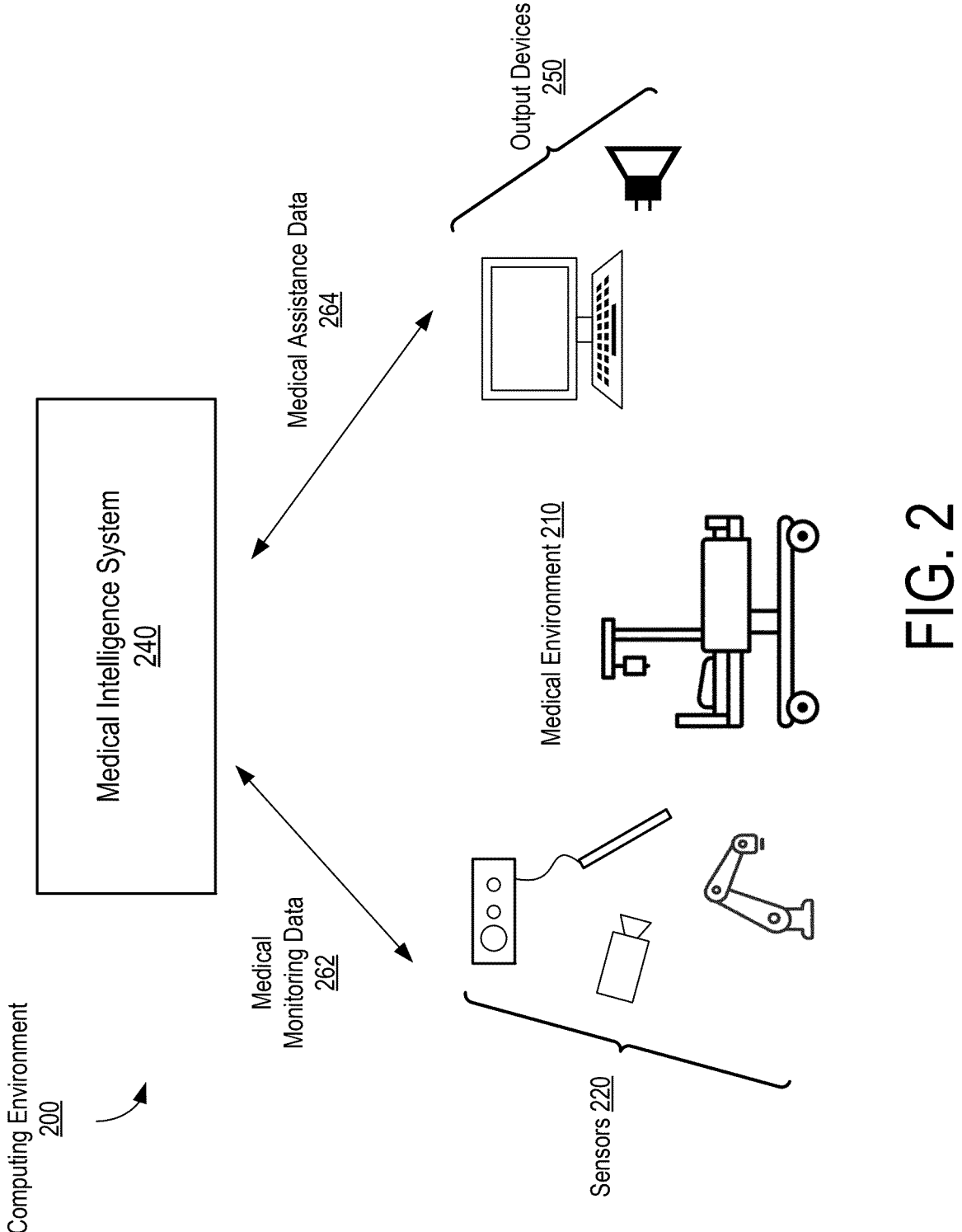
FIG. 2 is an example embodiment of a medical intelligence system.

FIG. 2 illustrates an example embodiment of a computing environment 200 for a medical intelligence system 240. A set of sensors 220 collect sensor input data for deriving real-time medical monitoring data 262 from the medical environment 210 in relation to an ongoing medical procedure. The medical monitoring data 262 may include the raw sensor data or data derived from processing the raw sensor data. Sensor data may include physiological or biological signals (such as pulse rate, blood pressure, body temperature, etc.), video, electrical signals representative of a state of a medical instruction, or other information. The sensors 220 may include, for example, one or more cameras, or other devices capable of sensing physiological or biological parameters associated with the patient (e.g., pulse, blood pressure, body temperature, etc.), conditions associated with the physicians, nurses, or other staff present in the medical environment 210, characteristics of medical tools or robotics devices (e.g., activation state, deployment state, temperature, energy, proximity to structures, etc.), or various environmental conditions associated with the medical environment. The sensors 220 may be standalone sensing devices or may be integrated with one or more medical instruments, robotic devices that performs or assists with aspects of the medical procedure, or other devices. Cameras or image sensors may include still image cameras, video cameras, 3D imaging devices, or a combination thereof. The cameras can include stationary cameras in the operating room or may include cameras integrated into medical instruments such as endoscopic cameras. The medical instruments (which may include integrated sensors 220) may include any instruments utilized in a medical procedure capable of producing signals (e.g., electrical, electronic, electro-mechanical, electro-magnetic, optical, etc.) indicative of an instrument or component state. For example, tracking sensors may track a position of a medical tool relative to the anatomy or may track other operating characteristics of the medical tool. A robotic device may include, for example, a robotic arm or other computer-controlled mechanical device that performs or assists with a medical procedure. The robotic device may be pre-programmed to perform a certain set of steps or tasks, and/or may be manually controlled by an operator.

The medical monitoring data 262 may be transmitted to the medical intelligence system 240. The medical intelligence system 240 may be implemented using on-site computing and/or storage systems, cloud computing and/or storage systems, or a combination thereof and may be implemented utilizing local or cloud-based servers, which may include physical and/or virtual machines, or a combination thereof. Cloud-based servers may include a private cloud systems, public cloud systems, hybrid public/private cloud systems, or a combination thereof. Accordingly, computing environment 200 and medical intelligence system 240 may be local, remote, and/or distributed with portions being local and portions remote, where the various system elements may be communicatively coupled over a network. The medical intelligence system 240 generates medical assistance data 264 based on the medical monitoring data 262 and one or more machine learning models determined to be useful in relation to the medical procedure. In an embodiment, the medical intelligence system 240 tracks a state of the medical procedure based on the medical monitoring data 262 and generates assistance data 264 relevant to the determined state. For example, the medical intelligence system 240 may detect that the procedure is at a particular step of a set of expected medical steps. Furthermore, the medical intelligence system 240 may detect if and when certain key events have occurred in the course of a medical procedure, which may include either expected events (e.g., the patient's blood pressure stabilizes) or unexpected events (e.g., the patient is experiencing abnormal amounts of bleeding). The medical assistance data 264 may include procedure-related information (e.g., data for guiding a human surgeon), or may include control and/or configuration-related information (e.g., data for controlling a robotic device or configuring a medical instrument). For example, in one embodiment, the medical assistance data 264 may determine a next step in a medical process and present instructions or critical tips associated with performing that step. The medical assistance data 264 may be in the form of text displayed on a screen, digital documents, a video clip, and/or an audio clip. Alternatively, the medical assistance data 264 may provide configuration and/or control information for a medical tool or robot that performs the determined step. In other examples, the medical assistance data 264 may assist with recordkeeping associated with the medical procedure. For example, the medical assistance data 264 may generate a description of the steps being performed, expected or unexpected events, relevant anatomies, or other information for documenting in association with a medical procedure. In another example, the medical assistance data 264 may include one or more determined billing codes associated with at least one event or sequence of events of the medical procedure.

In further examples, the medical intelligence system 240 may generate the medical assistance data 264 in response to a specific command (e.g., from the surgeon or other staff member in the medical environment 210). Here, the medical intelligence system 240 may receive a voice or text-based command for information and generate the medical assistance data 264 that is both responsive to the command and relevant to the current state of the medical procedure derived from the medical monitoring data 262. For example, a surgeon may issue a command such as "get me examples of a 'gastrectomy' step in a sleeve case where a female patient with low BMI is oozing." In response to the surgeon's command, the processing system 240 may then obtain context-specific examples (e.g., in the form of video and/or audio and/or other documentation) relevant to the command and based on the current detected state of the medical procedure and/or one or more other parameters such as sensory input, physiological parameters, and/or detected event information.

In another example, the medical assistance data 264 may automatically determine and/or infer parameters related to the medical procedure. For example, the medical assistance data 264 could characterize a complexity of the medical procedure based on the medical monitoring data 262. In another example, the medical assistance data 264 could characterize a safety aspect of the procedure based on the medical monitoring data 262 relative to expected baselines. The safety data may be used to train a model and gain insights about the particular set of steps employed, the staff members involved, or other data that can potentially improve patient safety in future procedures.

The output devices 250 obtain and present the medical assistance data 264. The output devices 250 may include, for example, one or more display systems (e.g., television display, computer display, projector, head-mounted augmented reality or virtual reality display, etc.), one or more audio output devices, or other output systems for presenting the medical assistance data 264. In an embodiment, the output devices 250 may include local processing for transforming the received medical assistance data 264 into a desired output format. For example, the output devices 250 may generate graphs, charts, video overlays, or other types of information displays to convey the medical assistance data 264. The output devices 250 may include (or may interface with) input devices for receiving inputs from a user such as a touch screen, microphone, joystick, mouse, keyboard, or other input devices.

The output devices 250 may present different medical assistance data 264 to different individuals associated with a medical procedure. For example, in the context of a surgical procedure, an output device 250 (or multiple different output devices 250) may present nurse-specific medical assistance data 264 to a nurse, physician-specific medical assistance data 164 to a physician, tech-specific medical assistance data 264 to a medical technician or assistant such as related to surgical robot setup, operation, fluidics, etc.

Figure 3:
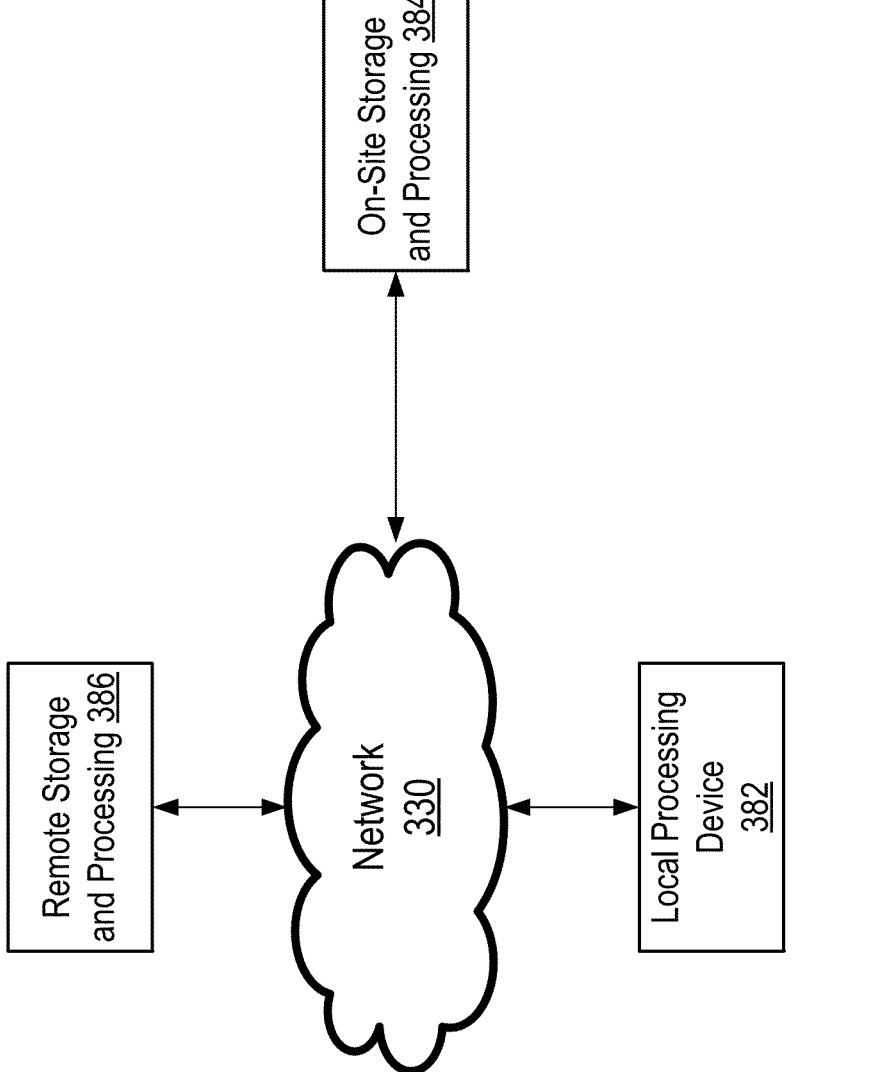
FIG. 3 is an example of a computing environment for implementing a medical intelligence system.

FIG. 3 illustrates an example of a computing and storage environment 300 associated with operation of the medical intelligence system 240. Here, the computing and storage environment 300 include a local processing device 382 (e.g., in the operating room or physically proximate to the operating room), on-site storage and processing 384 (e.g., in a hospital, unit, or medical facility), and remote storage and processing 386, which may be communicatively coupled by a network 330. On-site storage and processing 384 and remote storage and processing 386 may include cloud-based systems (e.g. public, private or hybrid public-private clouds) The network 330 may include one or more wired or wireless local area networks, one or more wired or wireless wide area networks (e.g., via wired or cellular communications), one or more peer-to-peer connections (e.g. over Wireless Personal Area Networks (WPANs) such as Bluetooth), and/or other communication channels for communicating between the local processing device 382, the on-site storage and processing 384, and the cloud storage and processing 386. In an embodiment, the network 330 may also provide communication between other elements shown in FIG. 2, such as the sensors 220 and the output devices 250. Communication channels for the exchange or personally identifiable or otherwise protected information may be secure and/or encrypted.

The local processing device 382 comprises one or more computing and/or storage devices local to the medical environment 210. For example, the local processing device 382 may be located within the room or on the same floor as a medical procedure being performed (e.g., in an operating room). The local processing device 382 may comprise, for example, an individual computing device such as a laptop, mobile device, or tablet. Alternatively, the local processing device 382 could comprise one or more servers. The on-site storage and processing 384 may include one or more computing and/or storage devices in a central location at a medical facility (e.g., a private cloud). The remote storage and processing 386 may include one more computing and/or storage devices at a geographically remote location (e.g., a remote cloud), or may be distributed between multiple physical locations. As described herein, different aspects of the medical intelligence system 240 may be physically implemented using any combination of one more local processing devices 382, on-site storage and processing 384, and/or remote storage and processing 386.

Figure 4:
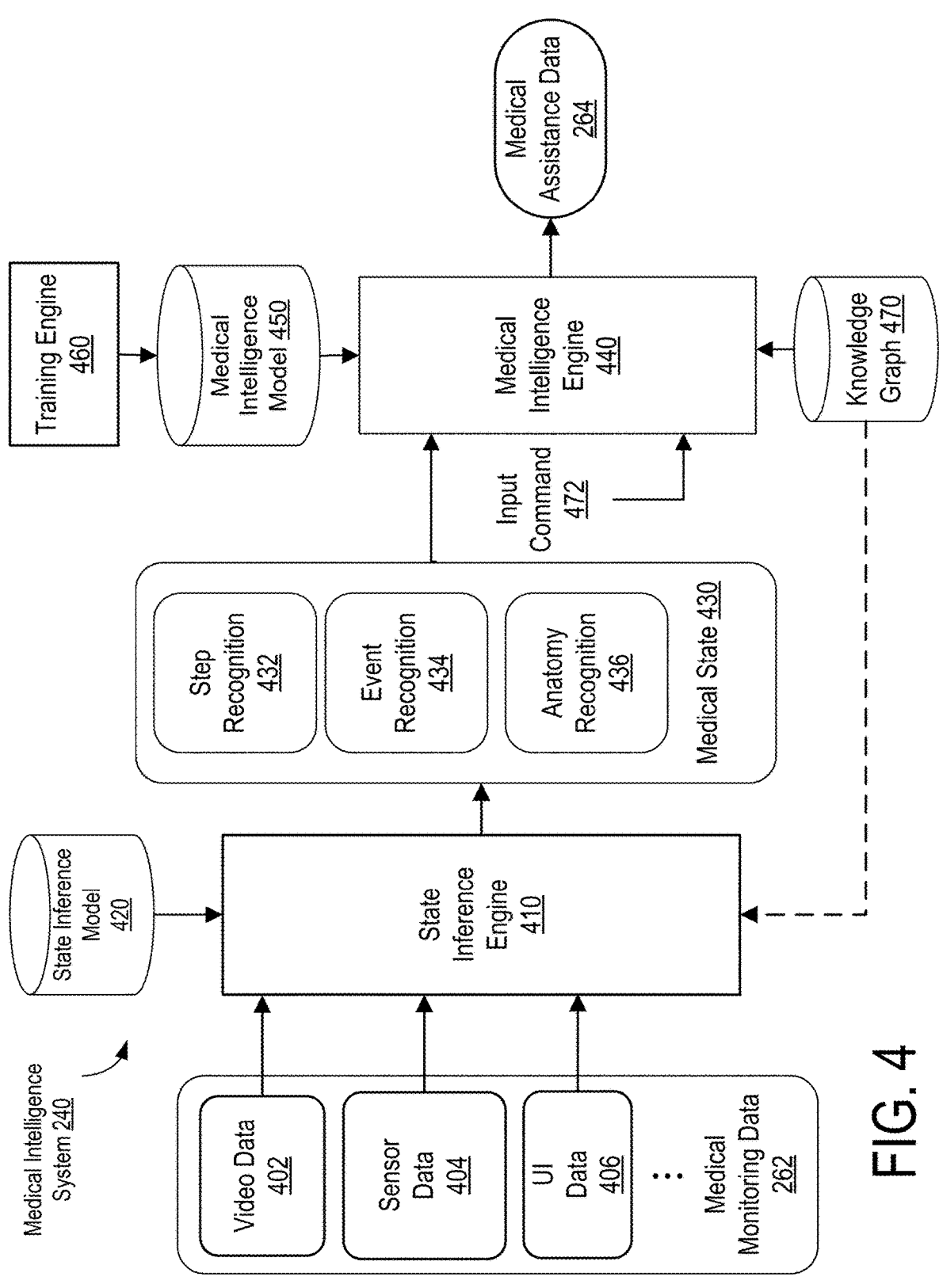
FIG. 4 is a first example embodiment of a medical intelligence system.

FIG. 4 is a block diagram illustrating example functional blocks associated with a medical intelligence system 240 including a state inference engine 410, a medical procedure intelligence engine 440, and a training engine 460. The state inference engine 410 receives the medical monitoring data 262 and may determine a medical state 430 based on a state inference model 420. The medical monitoring data 262 may include various types of data as described above, such as video 402, sensor inputs 404 (or data derived therefrom), user interface data 406, or other types of data indicative of a state of the medical procedure.

The medical state 430 may include, for example, step recognition 432, event recognition 434, and anatomy recognition 436. The step recognition 432 may determine a current step of the medical procedure being performed. In an embodiment, the step may be determined based in part on a sequence of steps associated with the medical procedure. In some instances, the sequence may have been predetermined based on input from the medical professional. Alternatively, the step recognition 432 may characterize an identified medical technique being performed without necessarily linking it to a predefined sequence of steps associated with a given medical procedure. For example, tool activation/deactivation, menu selections on a medical system (e.g., associated with a robotic or other medical device), detection of an organ, tissue, etc. may be used to determine a current or subsequent step. The step recognition 432 may include a single recognized step (e.g., representing the most likely step), or may include a set of possible steps each having different relative likelihoods.

The event recognition 434 records recognized events that occurred during the medical procedure. An event may be an expected event or an unexpected event. Events may relate to, for example, changes in patient medical state or other condition, use of a particular medical tool, actions by a physician or other staff member, actions performed by a robotic device, or other detectable occurrences in the context of the medical procedure. Events may be timestamped to indicate a time of occurrence of an event. Events may furthermore be indexed to steps or sub-steps detected in the step recognition 432 to associate the events with the steps or sub-steps taking place when they occur.

The anatomy recognition 436 represents patient anatomy associated with steps and/or events. For example, the anatomy recognition 436 may indicate where in the body a particular action was taken or condition was sensed. The anatomy recognition 436 may be indexed to an associated procedure, steps in that procedure, and/or events occurring during the procedure.

The state inference model 420 includes one or more machine learning models trained to determine the medical state data 430 based on the medical monitoring data 262. In an embodiment, the state inference model 420 may be trained using a supervised learning technique. For example, a time sequence of medical monitoring data 262 may be labeled with the corresponding medical state data 430 at each time instance and a machine learning algorithm is trained to determine the medical state data 430 based, in part, on the medical monitoring data 262. In an example embodiment, the state inference model 420 may include one or more convolutional neural networks (CNNs), recurrent neural networks (RNNs), other types of neural networks, recommendation engines, or different types of machine-learned models capable of achieving the functions described herein.

The state inference engine 410 may optionally determine the medical state 430 based in part on information in the knowledge graph 470 described below. Alternatively, the state inference engine 410 may determine the medical state 430 independently of the knowledge graph 470.

The medical procedure intelligence engine 440 receives the medical state 430 and an optional input query 472, and may determine relevant medical assistance data 264 based on a knowledge graph 470 and a medical intelligence model 450.

The knowledge graph 470 includes a database of medical information organized in a graph. The knowledge graph 470 may be used to represent multi-domain information at scale.

In some embodiments, a Resource Description Framework (RDF) may be used. For example, in one framework for a knowledge graph 470, nodes represent entities and edges between nodes indicate relationships including interactions between entities.

The knowledge graph 470 may evolve over time as more entities are indexed (thereby creating new nodes) and more relationships between entities are discovered (thereby creating additional edges). The knowledge graph 470 may be derived from a plurality of different information sources as described further below with respect to FIG. 8.

The medical intelligence model 450 includes one or more machine learning models trained to determine the medical assistance data 264 based on the medical state 430, the knowledge graph 470, and the optional input command 472. In an embodiment, the medical intelligence model 450 may be trained using a supervised learning technique in which medical state data 430 and information in the knowledge graph 470 is labeled using medical assistance data 264 that has been deemed useful at the current medical state. A machine learning algorithm then learns a mapping from the medical state 430 to the medical assistance data 264 utilizing the information in the knowledge graph 470. In an example embodiment, the medical intelligence model 450 may include one or more convolutional neural networks (CNNs), other types of neural networks, or different types of machine-learned models capable of achieving the functions described herein.

As described above, the medical intelligence engine 440 may optionally generate the medical assistance data 264 in part based on an explicit or implicit input command 472. The input command 472 may specify the type of information (e.g., video, tips, billing codes, documentation, etc.) to be provided in the medical assistance data 264 or may input an express request (e.g., in the form of a natural language question).

The training engine 460 trains the medical intelligence model 450. The training engine 460 may train the medical intelligence model 450 based on tracked histories of medical monitoring data 262, medical state 430, the medical assistance data 264 and other feedback relevant to determining usefulness of information that can be provided in a given context. For example, the training engine 460 may learn the relevance of historical medical assistance data 264 generated by the medical intelligence engine 440 from user selection and interaction (e.g., relevancy/utility input, length of interaction, watch time, etc.) with the medical assistance data 264 provided. The training engine 460 may thus observe based on subsequent medical state data 430 whether or not previously generated medical assistance data 264 was found relevant and useful and train the medical intelligence model 450 based on these observations. Here, medical assistance data 264 may be deemed as useful, for example, when a recommended next step is followed, when a recommended video is played, when recommended billing codes or documentation descriptions are approved, etc. In some embodiments, medical assistance data 274 that is not useful may be manually flagged by a staff member.

Figure 5:
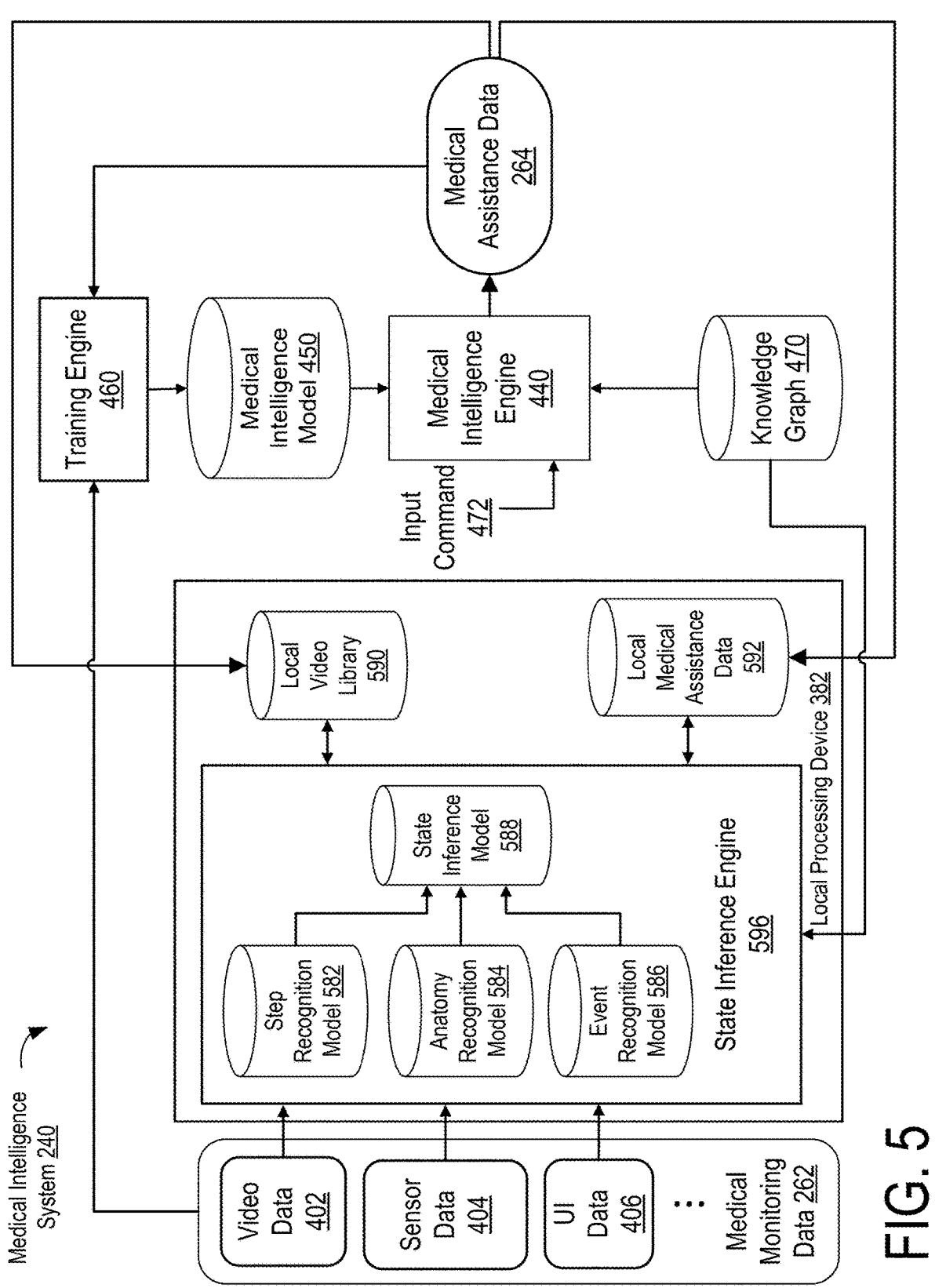
FIG. 5 is a second example embodiment of a medical intelligence system.

FIG. 5 is another example of a medical intelligence system 240. In this example, a local processing device 382 (which may be a local computing system in the operating room or medical facility) locally executes a state inference engine 596. The state inference engine 596 includes a step recognition model 582, an anatomy recognition model 584, and an event recognition model 586 for recognizing medical steps, anatomies, and events respectively from the medical monitoring data 262. The step recognition model 582, anatomy recognition model 584, and event recognition model 586 may form part of a state inference model 588 that infers the medical state as described above. The local processing device 382 may furthermore store (or have access to) a local video library 594 and local medical assistance data 592 storing videos and/or other assistance data that can be provided to a local output device 250 to assist the physician and/or staff during a medical procedure. The medical intelligence engine 440 operates as described above to generate the medical assistance data 264 based on the knowledge graph 270, the medical intelligence model 450, and an optional input command 472. A training engine 460 performs offline training of the medical intelligence model 450 based on a history of medical monitoring data 262, medical assistance data 264, or other inputs. In an embodiment, the training engine 460 may operate in a remote computing environment (e.g., the on-site storage and processing 384 and/or cloud storage and processing 386). Relevant medical assistance data 264 may be provided to the local processing device 382 for outputting to an output device 250 in the medical environment 210.

Figure 6:
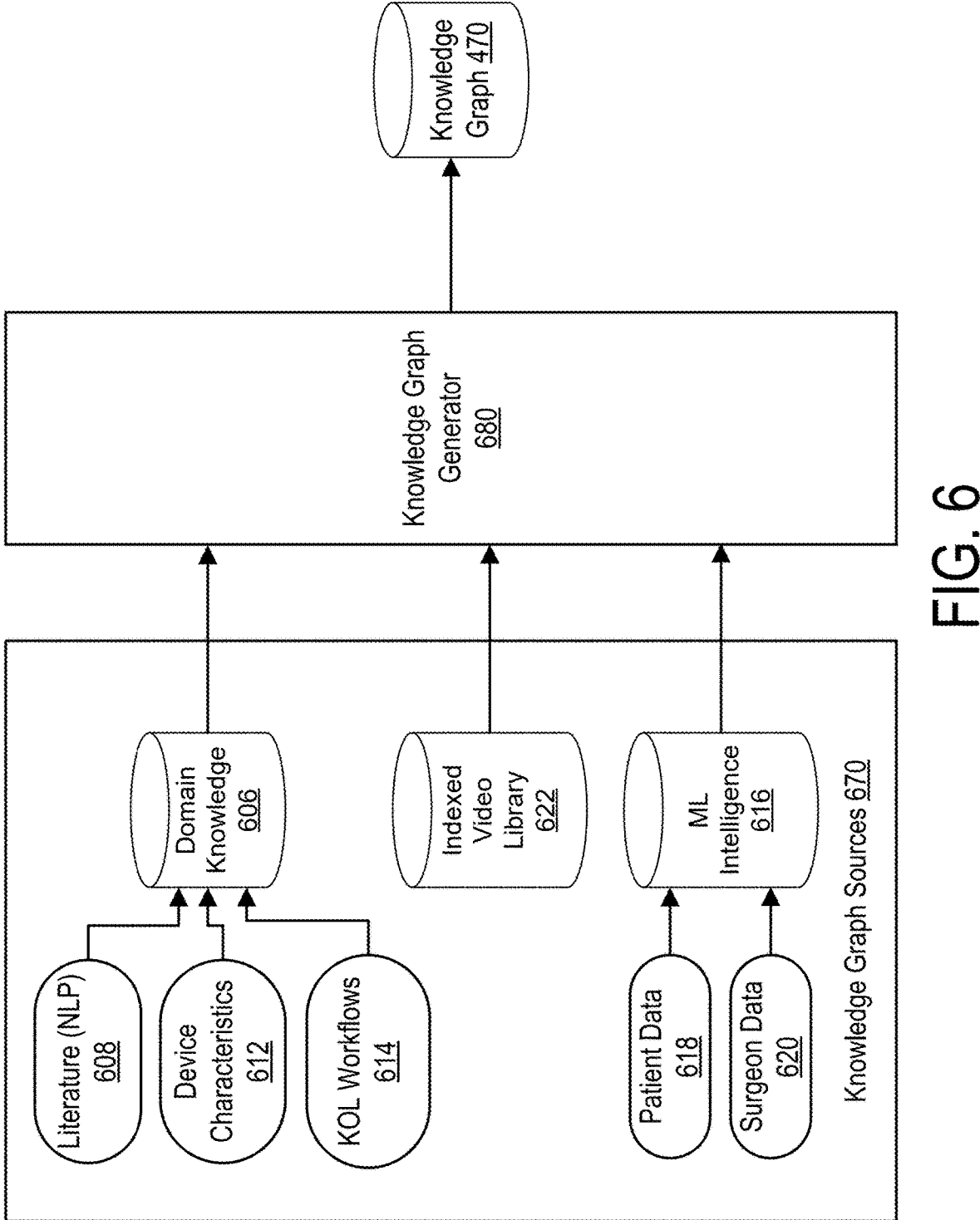
FIG. 6 is an example embodiment of a knowledge graph generator for generating a knowledge graph associated with a medical intelligence system.

FIG. 6 is an example embodiment of an architecture for generating a knowledge graph 470 based on a set of input sources 670. The input sources 670 may include domain knowledge database 606, an indexed video library 622, and machine learning intelligence database 616. The domain knowledge database 606 may be derived from sources such as published literature 608 (that may be indexed based on natural language processing), device characteristics 612, and Key Opinion Leader (KOL) workflows 614.

The published literature 608 may include databases or other data sources storing, for example, academic papers, medical or scientific journals, or other publications relevant to entities and relations in the knowledge graph 470. The device characteristics 612 include databases or other data sources storing information about the various sensors 220 that may be utilized in the medical environment 210. The KOL workflows 614 describe medical workflows recommended by various KOLs. For example, the KOL workflows 614 may be organized as indexed sets of steps for carrying out a medical procedure or other medical process. The literature 608, device characteristics 612, and KOL workflow 614 may be indexed in the domain knowledge database 606 in a common format.

The indexed video library 622 includes an indexed set of videos relevant to various medical procedures. The videos may include short clips or may include longer instructional videos. The videos may be indexed according to the relevant medical procedure or individual step of a procedure.

The machine learning intelligence database 616 may be derived from patient data 618 and surgeon data 620. The patient data 618 may include information such as patient identity, demographics, physical characteristics, medical history, and other available medical data. The surgeon data 620 may include information relating to different surgeons including, for example surgeon identity, educational background, employment, areas of expertise, experience, or other characteristics relevant to the surgeons.

The knowledge graph generator 680 organizes information from the various sources (e.g., the literature 608, indexed video library 622, and machine learning intelligence database 616) into a knowledge graph 470.

Examples of entities for inclusion in the knowledge graph 470 may include patient data (such as age, weight, height electrocardiogram (ECK/EKG) information, oxygen saturation (SPO2) information, breathing rate, pulse, clinical history, omics, medical plan, etc.), anatomy data (such as limb length, visceral fat, adhesions, tissue elasticity, etc.), imaging data (such as computed tomography (CT) images, x-ray images, magnetic resonance imaging (MRI) images, etc.), procedure data (such as phases, steps, tasks, and/or actions associated with a particular medical procedure), event data (such as bleeding events, oozing events, conversion to open events, etc.), device data (such as electrical characteristics, software characteristics, hardware characteristics, Bluetooth configuration, sensor information, etc.), video data (such as visible light videos or hyperspectral videos), surgeon data (such as experience level, specialty area, profile information, etc.), health system information, hospital information, outcome data (such as length of stay, medical site infection, re-admission, patient report post-medical outcomes, actigraphy steps, sleeping patterns, weight information, heart rate data, breathing rate data, SPO2 data, quality of life surveys, etc.)

Example of relations between entities in the knowledge graph 470 may be specified in the knowledge graph include, for example:

Procedure has Steps
Step has Tasks
Devices generate Data (e.g., Stapler generates Electrical Data)
Events represent timepoints during a procedure and form part of a Patient's Record
Medical Professional is associated with a hospital
Hospital is associated with Health System/Network where the underlined terms represent the relations and the capitalized terms represent the entities.

Figure 7:
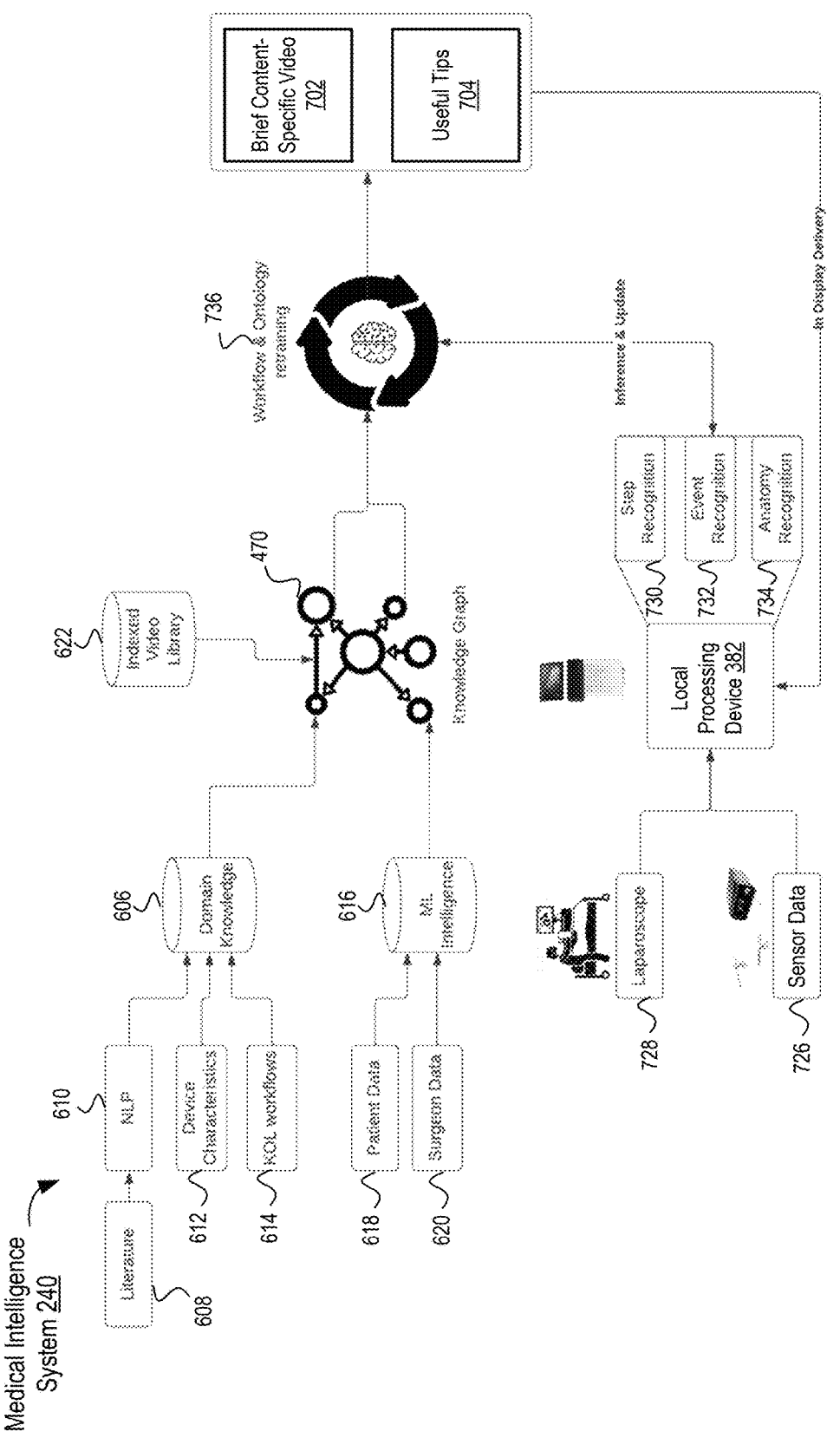
FIG. 7 is another example of a medical intelligence system for determining videos and critical tips relevant to a medical procedure.

FIG. 7 is another example of a medical intelligence system 240 incorporating the principles above. In this example, the medical intelligence system 240 determines context sensitive video clips (e.g., brief on-point video clips 702 based on a surgeon command and/or procedure state) and may provide useful real-time tips 704 relevant to a current state of a medical procedure. In the illustrated system, the domain knowledge database 606 receives various inputs from different sources including literature 608 that has been processed using natural language processing (NLP) 710 for parsing and indexing, device characteristics 612, and key opinion leader (KOL) workflows 614, as described above. A machine learning (ML) intelligence database 616 is also populated based on patient data 618 and surgeon data 620. The knowledge graph 470 is generated based on the information in the domain knowledge database 606, the ML intelligence database 616 and the indexed video library 622. A local processing device 382 furthermore collects and processes sensor data 726, laparoscope data 728, or other medical data to generate results relating to step recognition 730, event recognition 732, and anatomy recognition 734 as described above. A workflow and ontology retraining engine 736 access the knowledge graph 470 to generate outputs such as the context-specific videos 702, useful tips 704, or other medical assistance data 264, which may be provided for display on the local processing device 382 or an attached display device. The workflow and ontology retraining engine 736 furthermore may generate inferences used in the step recognition 730, event recognition 732, and anatomy recognition 734 steps, which may also update underlying machine learning models used by the workflow and ontology retraining engine 736.

Figure 8:
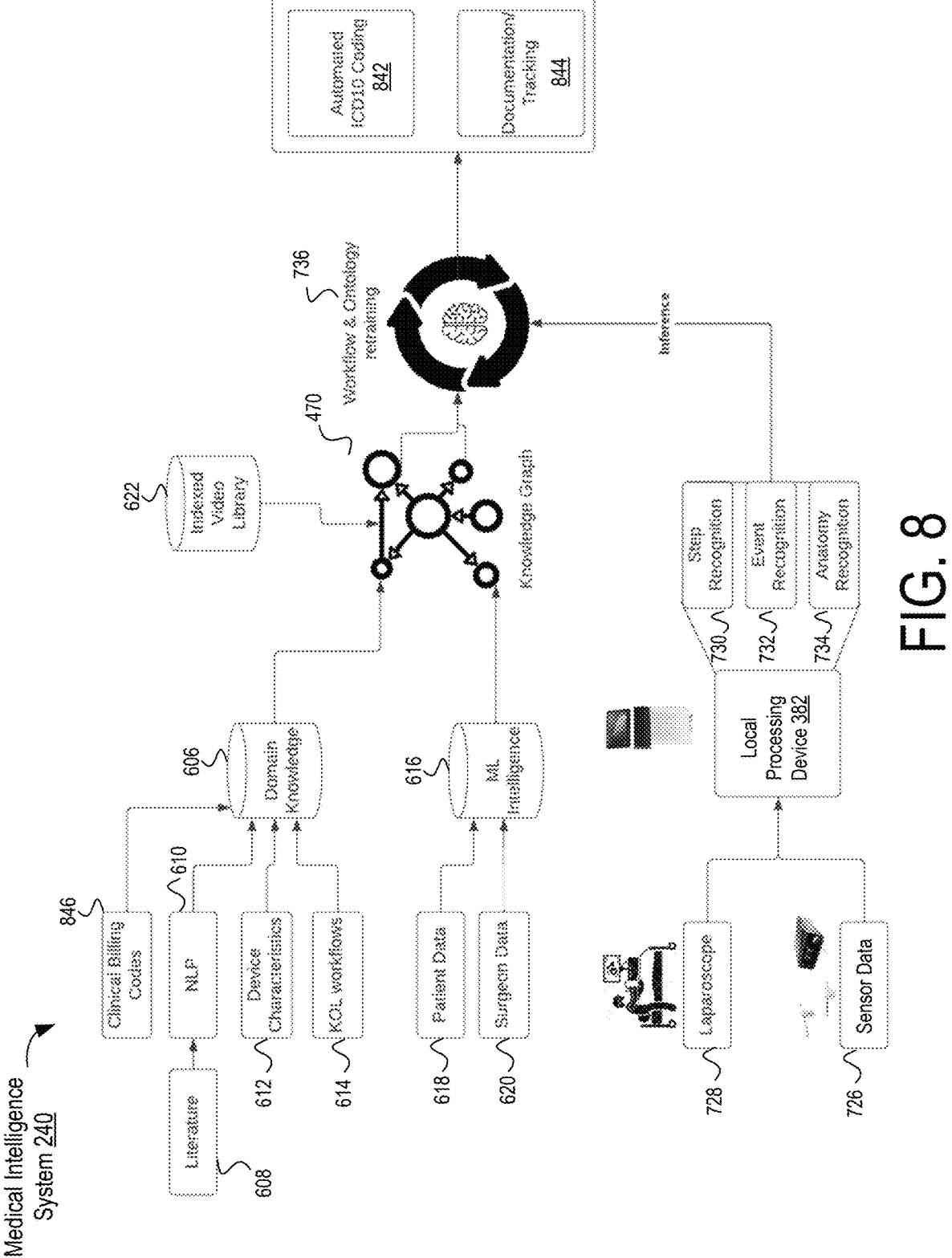
FIG. 8 is another example of a medical intelligence system for determining billing codes and documentation/tracking information associated with a medical procedure.

FIG. 8 is another example of a medical intelligence system 240 incorporating the principles above. In this example, the medical intelligence system 240 determines medical codes 842 (e.g., International Classification of Diseases 10th revision (ICD10) coding) and documentation/ tracking information 844 relevant to a determined state of a medical procedure, which may additionally be based on clinical billing codes 846 stored to the domain knowledge database 606.

Figure 9:
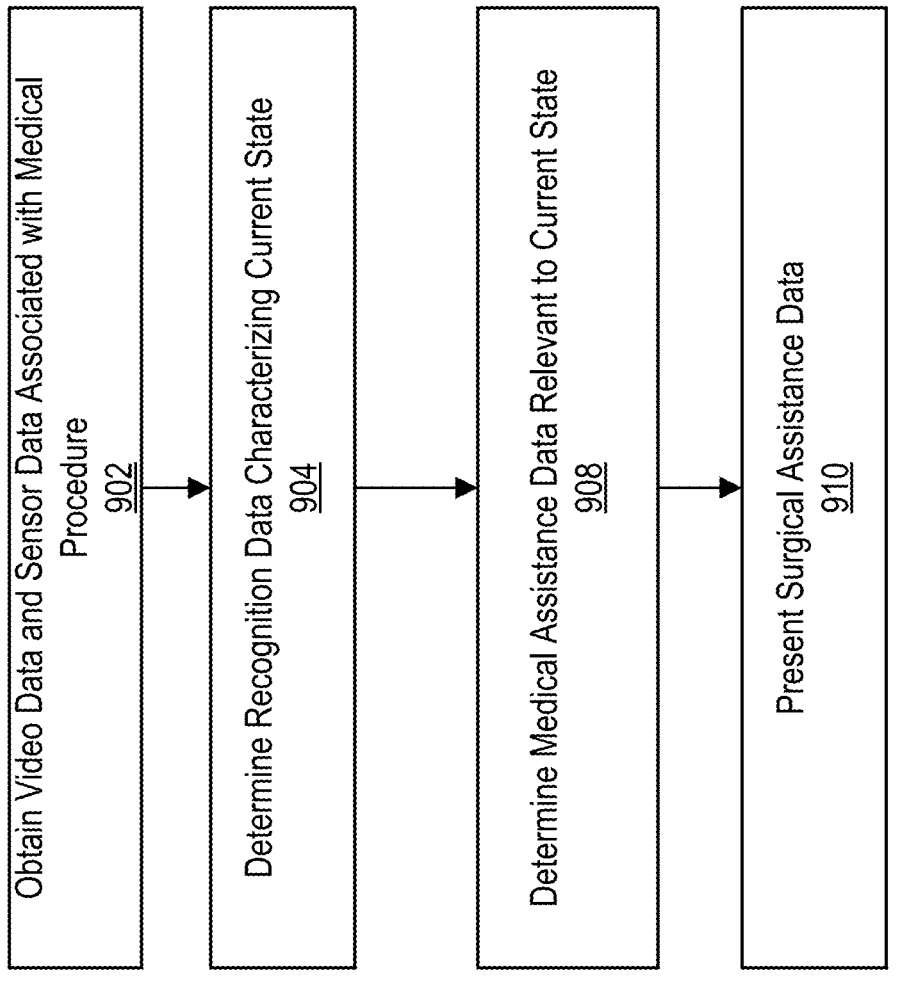
FIG. 9 is a flowchart illustrating an example embodiment of a process for generating medical assistance data associated with a medical procedure.

FIG. 9 is an example embodiment of a process for generating medical assistance data 264 associated with a medical procedure. The medical intelligence system 240 obtains 902 video data and/or sensor data associated with an ongoing medical procedure. The medical intelligence system 240 determines 904 recognition data characterizing a current state of the medical procedure (e.g., based on application of a state inference model 420). The medical intelligence system 240 determines 908 medical assistance data relevant to the current state based on a learned medical intelligence model 450 and knowledge graph 470. The medical intelligence system 240 then presents 910 the medical assistance data 264. The medical assistance data 264 may represent, for example, video or text instructions or tips, relevant billing codes or documentation, characterizations of the medical process, or other data determined to be relevant to the medical procedure.

Embodiments of the described computing environment 200 for a medical intelligence system 240 and corresponding processes may be implemented by one or more computing systems. The one or more computing systems include at least one processor and a non-transitory computer-readable storage medium storing instructions executable by the at least one processor for carrying out the processes and functions described herein. The computing system may include distributed network-based computing systems in which functions described herein are not necessarily executed on a single physical device. For example, some implementations may utilize cloud processing and storage technologies, virtual machines, or other technologies.

The foregoing description of the embodiments has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe the embodiments in terms of algorithms and symbolic representations of operations on information. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. Embodiments may also relate to an apparatus for performing the operations herein. This apparatus may be specially constructed for the required purposes, and/or it may include a general-purpose computing device selectively activated or reconfigured by a computer program stored in the computer. Such a computer program may be stored in a tangible non-transitory computer readable storage medium or any type of media suitable for storing electronic instructions and coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope is not limited by this detailed description, but rather by any claims that issue on an application based hereon. Accordingly, the disclosure of the embodiments is intended to be illustrative, but not limiting, of the scope of the invention, which is set forth in the following claims.

The invention claimed is:

1. A method for providing intelligent medical assistance, the method comprising:

connecting to a remote storage and processing system that is remote from medical site of a medical procedure, wherein the remote storage and processing system maintains a knowledge graph including a database of medical information that dynamically updates from multiple disparate network data sources as new information becomes available, wherein the knowledge graph is organized into a graph data structure that stores nodes representing entities and edges between nodes indicating relationships between the entities;

obtaining during the medical procedure by a local processing device local to the medical site, medical monitoring data including at least video data capturing the medical procedure and sensor data from one or more sensors associated with the medical procedure;

processing, by the local processing device local to the medical site, the medical monitoring data through a state inference engine that includes a step recognition model for recognizing a current step of the medical procedure, an anatomy recognition model for recognizing anatomy of a patient during the medical procedure, an event recognition model for recognizing events that occur during the medical procedure, and a state inference model that infers a current state of the medical procedure based on at least the current step, the anatomy, and the events, wherein the step recognition model, the anatomy recognition model, the event recognition model, and the state inference model each comprise independently trained machine learning models;

communicating, via a network, the current state of the medical procedure to the remote storage and processing system;

obtaining over the network, from a medical intelligence engine operating at the remote storage and processing system, medical assistance data relevant to the current state of the medical procedure that is generated based on machine learning inferences obtained from a medical intelligence model and based on accessing the knowledge graph; and outputting, via an output device coupled to the local processing device, the medical assistance data.

2. The method of claim 1, wherein the medical intelligence engine generates the medical assistance data by:

determining a recommended next step in the medical procedure that follows from the current state; and obtaining, based on the recommended next step, a video clip associated with the recommended next step.

3. The method of claim 1, wherein the medical intelligence engine generates the medical assistance data by:

determining a recommended next step in the medical procedure that follows from the current state; and obtaining, based on the recommended next step, documents or audio instructions associated with the recommended next step.

4. The method of claim 1, wherein the medical intelligence engine generates the medical assistance data by:

identifying a medical billing code associated with the current state; and associating the medical billing code with a billing record in an electronic patient file.

5. The method of claim 1, wherein the medical intelligence engine generates the medical assistance data by:

identifying a relevant form description associated with the current state of the medical procedure; and associating the relevant form description with an electronic patient file.

6. The method of claim 1, wherein the remote storage and processing system operates to:

train the medical intelligence model based on a history of medical procedure states associated with prior medical procedures and input responsive to prior medical assistance data.

7. The method of claim 1, wherein the knowledge graph comprises entities and relations derived from at least one of: an indexed video library, domain knowledge including medical literature, device characteristics, and key opinion leader workflows, and machine learning intelligence including patient data and surgeon data.

8. A non-transitory computer-readable storage medium storing instructions for providing medical intelligence data, the instructions when executed by one or more processors causing the one or more processors to perform steps including:

connecting to a remote storage and processing system that is remote from medical site of a medical procedure, wherein the remote storage and processing system maintains a knowledge graph including a database of medical information that dynamically updates from multiple disparate network data sources as new information becomes available, wherein the knowledge graph is organized into a graph data structure that stores nodes representing entities and edges between nodes indicating relationships between the entities;

obtaining during the medical procedure by a local processing device local to the medical site, medical monitoring data including at least video data capturing the medical procedure and sensor data from one or more sensors associated with the medical procedure;

processing, by the local processing device local to the medical site, the medical monitoring data through a state inference engine that includes a step recognition model for recognizing a current step of the medical procedure, an anatomy recognition model for recognizing anatomy of a patient during the medical procedure, an event recognition model for recognizing events that occur during the medical procedure, and a state inference model that infers a current state of the medical procedure based on at least the current step, the anatomy, and the events, wherein the step recognition model, the anatomy recognition model, the event recognition model, and the state inference model each comprise independently trained machine learning models;

communicating, via a network, the current state of the medical procedure to the remote storage and processing system;

obtaining over the network, from a medical intelligence engine operating at the remote storage and processing system, medical assistance data relevant to the current state of the medical procedure that is generated based on machine learning inferences obtained from a medical intelligence model and based on accessing the knowledge graph; and outputting, via an output device coupled to the local processing device, the medical assistance data.

9. The non-transitory computer-readable storage medium of claim 8, wherein the medical intelligence engine generates the medical assistance data by:

determining a recommended next step in the medical procedure that follows from the current state; and obtaining, based on the recommended next step, a video clip associated with the recommended next step.

10. The non-transitory computer-readable storage medium of claim 8, wherein the medical intelligence engine generates the medical assistance data by:

determining a recommended next step in the medical procedure that follows from the current state; and obtaining, based on the recommended next step, documents or audio instructions associated with the recommended next step.

11. The non-transitory computer-readable storage medium of claim 8, wherein the medical intelligence engine generates the medical assistance data by:

identifying a medical billing code associated with the current state; and associating the medical billing code with a billing record in an electronic patient file.

12. The non-transitory computer-readable storage medium of claim 8, wherein the medical intelligence engine generates the medical assistance data by:

identifying a relevant form description associated with the current state of the medical procedure; and associating the relevant form description with an electronic patient file.

13. The non-transitory computer-readable storage medium of claim 8, wherein the remote storage and processing system operates to:

train the medical intelligence model based on a history of medical procedure states associated with prior medical procedures and input responsive to prior medical assistance data.

14. The non-transitory computer-readable storage medium of claim 8, wherein the knowledge graph comprises entities and relations derived from at least one of: an indexed video library, domain knowledge including medical literature, device characteristics, and key opinion leader workflows, and machine learning intelligence including patient data and surgeon data.

15. A computer system comprising:

one or more processors; and a non-transitory computer-readable storage medium storing instructions for providing medical intelligence data, the instructions when executed by the one or more processors causing the one or more processors to perform steps including:

connecting to a remote storage and processing system that is remote from medical site of a medical procedure, wherein the remote storage and processing system maintains a knowledge graph including a database of medical information that dynamically updates from multiple disparate network data sources as new information becomes available, wherein the knowledge graph is organized into a graph data structure that stores nodes representing entities and edges between nodes indicating relationships between the entities;

obtaining during the medical procedure by a local pro-
cessing device local to the medical site, medical moni-
toring data including at least video data capturing the
medical procedure and sensor data from one or more
sensors associated with the medical procedure;
processing, by the local processing device local to the
medical site, the medical monitoring data through a
state inference engine that includes a step recognition
model for recognizing a current step of the medical
procedure, an anatomy recognition model for recog-
nizing anatomy of a patient during the medical proce-
dure, an event recognition model for recognizing
events that occur during the medical procedure, and a
state inference model that infers a current state of the
medical procedure based on at least the current step, the
anatomy, and the events, wherein the step recognition
model, the anatomy recognition model, the event rec-
ognition model, and the state inference model each
comprise independently trained machine learning mod-
els;
communicating, via a network, the current state of the
medical procedure to the remote storage and processing
system;
obtaining over the network, from a medical intelligence
engine operating at the remote storage and processing
system, medical assistance data relevant to the current
state of the medical procedure that is generated based on machine learning inferences obtained from a medi-
cal intelligence model and based on accessing the
knowledge graph; and
outputting, via an output device coupled to the local
processing device, the medical assistance data.
16. The computer system of claim 15, wherein the medi-
cal intelligence engine generates the medical assistance data
by:
determining a recommended next step in the medical
procedure that follows from the current state; and
obtaining, based on the recommended next step, a video
clip associated with the recommended next step.
17. The computer system of claim 15, wherein the medi-
cal intelligence engine generates the medical assistance data
by:
determining a recommended next step in the medical
procedure that follows from the current state; and
obtaining, based on the recommended next step, docu-
ments or audio instructions associated with the recom-
mended next step.
18. The computer system of claim 15, wherein the medi-
cal intelligence engine generates the medical assistance data
by:
identifying a medical billing code associated with the
current state; and
associating the medical billing code with a billing record
in an electronic patient file.

* * * * *